United States Patent

Nishimura et al.

[11] Patent Number: 5,973,168
[45] Date of Patent: Oct. 26, 1999

[54] PREPARATION PROCESS OF PHTHALIDE COMPOUND

[75] Inventors: Takeshi Nishimura; Masaru Wada; Yoshinobu Kanemura, all of Fukuoka-ken; Satoshi Nakao, Osaka-fu; Mansuke Matsumoto, Hyogo-ken, all of Japan

[73] Assignees: Mitsui Chemicals, Inc., Tokyo; Yamamoto Chemicals, Osaka-fu, both of Japan

[21] Appl. No.: 09/094,559

[22] Filed: Jun. 15, 1998

[30] Foreign Application Priority Data

Jun. 18, 1997 [JP] Japan ..................... 9-161006

[51] Int. Cl.⁶ .............................................. C07D 307/885
[52] U.S. Cl. ................................................... 549/309
[58] Field of Search .............................................. 549/309

[56] References Cited

U.S. PATENT DOCUMENTS 4,271,075  6/1981  Nagata et al. ..................... 549/309

FOREIGN PATENT DOCUMENTS 0008118  2/1980  European Pat. Off. .
0291600  11/1988  European Pat. Off. .

*Primary Examiner*—Bernard Dentz
*Attorney, Agent, or Firm*—Burns, Doane, Swecker & Mathis, L.L.P.

[57] ABSTRACT

A process for preparing a phthalide compound represented by the formula (1):

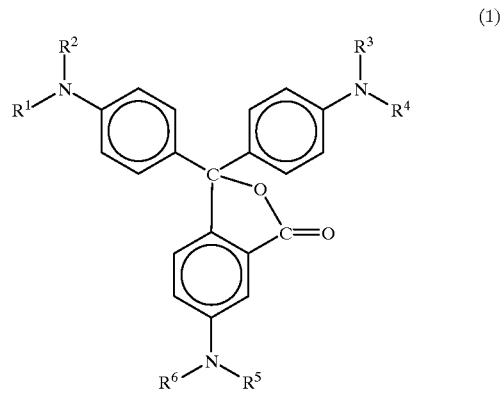

wherein $R^1$, $R^2$, $R^3$, $R^4$, $R^5$ and $R^6$ are individually an alkyl group, and $R^1$ and $R^2$, $R^3$ and $R^4$, and $R^5$ and $R^6$ can respectively bond to each other to form a heterocyclic ring together with a nitrogen atom, comprising oxidizing a triphenylmethane compound represented by the formula (2)

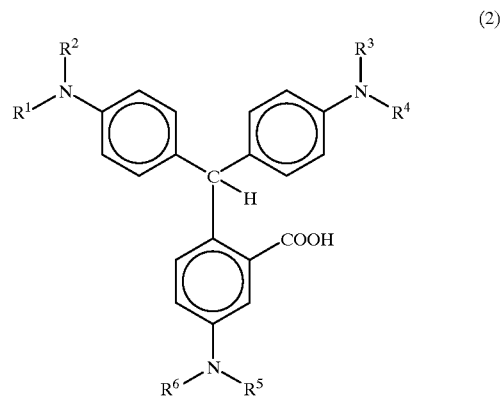

wherein $R^1$, $R^2$, $R^3$, $R^4$, $R^5$ and $R^6$ are the same as above, is oxidized in the presence of activated carbon in an aqueous solvent by an oxidizing agent.

The process can provide a fast reaction that produces a high purity product with high yield.

7 Claims, No Drawings

PREPARATION PROCESS OF PHTHALIDE COMPOUND

BACKGROUND OF THE INVENTION

1. Field of the Invention

The present invention relates to a preparation process of a phthalide compound useful as a color former of color-developing recording materials.

2. Related Art of the Invention

A 3,3-bisarylphthalide compound having amino groups, 3,3-bis(4-dimethylaminophenyl)-6-dimethylaminophthalide(crystal violet lactone) in particular, is widely used for pressure sensitive copying papers and thermal recording papers as a color former which develops blue color.

Japanese Laid-Open Patent SHO 62-184061, SHO 55-120562 and HEI 02-47160 have described processes for preparing a phthalide compound by oxidizing a triarylmethene compound. However, these preparation processes have led to problems. For example, the reaction system increases alkali concentration with the progress of the reaction in these preparation processes and causes problems of permanently remaining unreacted raw materials. Further, a metal compound is added in order to accelerate the reaction and remains in the waste water in the step of filtering and washing the phthalide reaction product. Such residual materials have caused problems of increasing the cost of waste water disposal.

SUMMARY OF THE INVENTION

One object of the invention is, in the preparation of a phthalide compound from a triphenylmethane compound by oxidation, to provide an economical preparation process which progresses the reaction very quickly and has no waste water disposal problem after terminating the reaction.

As a result of an intensive investigation in order to accomplish the above object, the present inventors have found that the reaction progresses smoothly in the presence of activated carbon and can go to completion within a short time. Thus the present invention has been achieved.

That is, one aspect of the invention is a preparation process of a phthalide compound represented by the formula (1):

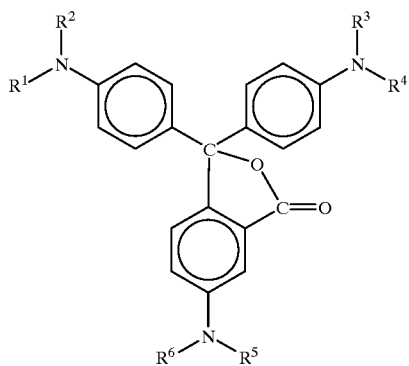

(1)

wherein $R^1$, $R^2$, $R^3$, $R^4$, $R^5$ and $R^6$ are individually an alkyl group, and $R^1$ and $R^2$, $R^3$ and $R^4$, and $R^5$ and $R^6$ can respectively bond to each other to form a heterocyclic ring together with a nitrogen atom, comprising oxidizing a triphenylmethane compound represented by the formula (2):

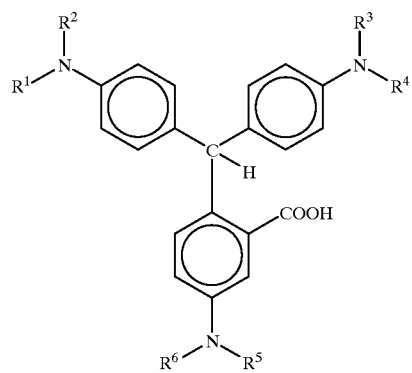

(2)

wherein $R^1$, $R^2$, $R^3$, $R^4$, $R^5$ and $R^6$ are individually an alkyl group, and $R^1$ and $R^2$, $R^3$ and $R^4$, and $R^5$ and $R^6$ can respectively bond to each other to form a heterocyclic ring together with a nitrogen atom, by an oxidizing agent in an aqueous solvent in the presence of activated carbon.

The present invention can provide a process for preparing a phthalide compound in a short time with a high yield by oxidizing a triphenylmethane compound (leuco compound).

DETAILED DESCRIPTION OF THE INVENTION

The preparation process of the invention will hereinafter be illustrated in detail.

The substituents $R^1$, $R^2$, $R^3$, $R^4$, $R^5$ and $R^6$ in the formulas (1) and (2) are individually an alkyl group, and these alkyl groups can also form a heterocyclic ring together with a nitrogen atom by respectively bonding $R^1$ and $R^2$, $R^3$ and $R^4$, and $R^5$ and $R^6$ to each other. These alkyl groups have preferably 1 to 8 carbon atoms, more preferably 1 to 4 carbon atoms, when $R^1$ to $R^6$ are an alkyl group. Specific alkyl groups include, for example, methyl, ethyl, n-propyl, iso-propyl, n-butyl, iso-butyl, sec-butyl, n-pentyl, iso-pentyl, neo-pentyl, n-hexyl, iso-hexyl, n-heptyl, n-octyl and 2-ethyl hexyl. Representative heterocyclic rings which are obtained by respectively bonding $R^1$ and $R^2$, $R^3$ and $R^4$, and $R^5$ and $R^6$ and by forming together with the nitrogen atom include, for example, piperidino, piperazino, pyrrolidino and morpholino. The piperidino group and pyrrolidino group are preferred.

Specific triphenylmethane compounds (hereinafter, abbreviation is leuco compound) which can be used in the invention and are represented by the formula (2) include preferably 2-[4,4'-bis(dimethylamino)benzhydryl]-5-dimethylaminobenzoic acid, 2-[4,4'-bis(diethylamino)benzhydryl]-5-dimethylaminobenzoic acid, 2-[4,4'-bis(dimethylamino)benzhydryl]-5-diethylaminobenzoic acid, 2-[4,4'-bis(ethylmethylamino)benzhydryl]-5-dimethylaminobenzoic acid, 2-[4,4'-bis(diethylamino)benzhydryl]-5-diethylaminobenzoic acid, 2-[4,4'-bis(diethylamino)benzhydryl]-5-diethylaminobenzoic acid, 2-[4,4'-bis(di-n-propylamino)benzhydryl]-5-dimethylaminobenzoic acid, 2-[4,4'-bis(di-iso-propylamino)benzhydryl]-5-dimethylaminobenzoic acid, 2-[4,4'-bis(di-n-butylamino)benzhydryl]-5-dimethylaminobenzoic acid,
2-[4,4'-bis(di-iso-butylamino)benzhydryl]-5-dimethylaminobenzoic acid,
2-[4,4'-bis(di-n-butylamino)benzhydryl]-5-diethylaminobenzoic acid,
2-(4-di-n-butylamino-4'-diethylamino)benzhydryl-5-diethylaminobenzoic acid,
2-[4,4'-bis(di-n-butylamino)benzhydryl]-5-di-n-butylaminobenzoic acid,
2-[4,4'-bis(di-sec-butylamino)benzhydryl]-5-dimethylaminobenzoic acid,
2-[4,4'-bis(pyrrolidino)benzhydryl]-5-dimethylaminobenzoic acid, and
2-[4,4'-bis(piperidino)benzhydryl]-5-dimethylaminobenzoic acid.

Representative examples of phthalide compounds which are represented by the formula (1) and can be prepared in the invention from the above corresponding compound represented by the formula (2), include
3,3-bis(4-dimethylaminophenyl)-6-dimethylaminophthalide,
3,3-bis(4-diethylaminophenyl)-6-dimethylaminophthalide,
3,3-bis(4-dimethylaminophenyl)-6-diethylaminophthalide,
3,3-bis(4-ethylmethylaminophenyl)-6-diethylaminophthalide,
3,3-bis(4-diethylaminophenyl)-6-diethylaminophthalide,
3-(4-diethylaminophenyl)-3-(4-dimethylaminophenyl)-6-diethylaminophthalide,
3,3-bis(4-di-n-propylaminophenyl)-6-dimethylaminophthalide,
3,3-bis(4-di-iso-propylaminophenyl)-6-dimethylaminophthalide,
3,3-bis(4-di-n-butylaminophenyl)-6-dimethylaminophthalide,
3,3-bis(4-di-n-butylaminophenyl)-6-dimethylaminophthalide,
3,3-bis(4-di-iso-butylaminophenyl)-6-dimethylaminophthalide,
3-(4-di-n-butylaminophenyl)-3-(4-diethylaminophenyl)-6-diethylaminophthalide,
3,3-bis(4-di-n-butylaminophenyl)-6-di-n-butylaminophthalide,
3,3-bis(4-di-sec-butylaminophenyl)-6-dimethylaminophthalide,
3,3-bis(4-pyrrolidinophenyl)-6-dimethylaminophthalide, and
3,3-bis(4-piperidinophenyl)-6-dimethylaminophthalide.

The term "aqueous solvent" in the invention refers to a solvent containing 80% by weight or more of water, and includes water and a solvent mixture of water and an organic solvent. Organic solvents which can be used as a mixture with water are preferably isopropyl alcohol, n-butyl alcohol and other alcoholic solvents, and benzene, toluene and other aromatic hydrocarbon solvents. A solvent mixture containing 20% by weight or more of organic solvent is liable to the reaction velocity, and thus preferred solvents are water and a solvent mixture containing 80% by weight or more of water. The amount for use of these solvents is 2 to 20 times by weight, preferably 5 to 15 times by weight of the leuco compound.

Oxidizing agents which can be preferably used in the invention are one or more agents selected from air, oxygen, hydrogen peroxide and a mixture of oxygen and an inert gas. More preferred oxidizing agents are air, oxygen and a mixture of air and oxygen. These oxidizing agents are introduced into the reaction mass at atmospheric pressure or under increased pressure.

When oxygen or an oxygen containing gas is used for the oxidizing agent, the oxidizing agent is required in an oxygen amount equimolar or more for the triphenylmethane compound of the formula (2) (leuco compound) which is used in the reaction. Hydrogen peroxide is preferably used in an amount 1 to 1.2 times by mole of the leuco compound used in the reaction. Less than equimolar amount of the oxidizing agent cannot complete the reaction. On the other hand, when the amount of hydrogen peroxide exceeds 1.2 moles, a large amount of decomposition products is formed. When oxygen or the oxygen containing gas is used in combination with hydrogen peroxide, hydrogen peroxide is preferably used in an equimolar amount or less for the leuco compound used in the reaction. The reason is that oxygen does not generate a large amount of the decomposition products even though used in a large quantity, whereas hydrogen peroxide increases the decomposition products in the presence of a large quantity.

Activated carbons which can be used in the invention are powdery carbon, granulated carbon, globular carbon, crushed carbon and pelletized carbon. For example, CARBORAFIN-SHIRASAGI Series: A, B, C, G, M, P, S, DC, KL, W, EH, X-7000 and X-7100 (manufactured by Takeda Chemical Ind. Co.); TAIKOH ACTIVATED CARBON: SGF, SA-1000, K, KA, A, K1, AP, RC, S5, P, W, SGS, SGA, SG, SGP, CG48B, CW830B, CW350B, CW612G and CW816G (manufactured by Futamura Chemical Ind. Co.); PM Series: PM-PA, PM-PW, PM-PW1, PM-WA, PM-KI, PM-YO, PM-KS, PM-MO, PM-AA, PM-PE, PM-CR, PM-WA, PM-SX, PM-FZ and PM-SAY (manufactured by Mitsui Pharmaceutical Ind. Co.); and CAL, CPG, APC, F-300 and F-400 (manufactured by Toyo Calgon Co.).

Further, activated carbons spread or carried on a metallic compound, for example, FCA, Sulfsorb (manufactured by Toyo Calgon Co.); palladium carried carbon or platinum carried carbon, may be used in the present invention.

Catalytic activity can be observed also on other grades so long as the activated carbon is prepared from wood, charcoal, coconut husk or coal. Particularly excellent catalytic activity is found on SHIRASAGI-A, B, C, D, M and P; APC and CPG.

The activated carbon exhibits higher effect with an increased amount of use on the acceleration of oxidation. However, the amount for use of the activated carbon is preferably 5 to 100% by weight of the leuco compound in view of workability in the step of activated carbon removal and economy.

Acid or base can be used in the invention in order to smoothly conduct the reaction.

Exemplary acids which can be used include hydrochloric acid, sulfuric acid, nitric acid and other mineral acids; and p-toluenesulfonic acid, methanesulfonic acid, acetic acid, formic acid and other organic acids.

Exemplary bases which can be used include sodium hydroxide, potassium hydroxide, sodium carbonate, potassium carbonate, sodium hydrogen carbonate, potassium hydrogen carbonate, sodium methylate, potassium methylate, sodium ethylate, potassium ethylate and other inorganic bases; and pyridine, triethylamine, 1,8-diazabicyclo[5.4.0]-7-undecene, 1,5-diazabicyclo[4.3.0]-5-nonene, 1,4-diazabicyclo[2.2.2]octane, guanidine and other organic bases.

The process of the invention can be carried out either at atmospheric pressure or under increased pressure.

The reaction temperature is preferably 40 to 120° C., more preferably 70 to 100° C.

The reaction time depends upon the reaction temperature, reaction pressure and species and amount of activated carbon, and is 3 to 20 hours when the reaction is carried out at 90 to 95° C. at the atmospheric pressure. The time can be reduced to 1 to 6 hours under increased pressure at the same temperature.

When foaming is violent in the course of the reaction, the foaming can be reduced by addition of a small amount of a 2-ethylhexanol or polyethylene glycol based antifoaming agent; isopropyl alcohol, n-butyl alcohol and other alcohols; or benzene, toluene and other aromatic hydrocarbon solvents.

The phthalide compound thus obtained can be further purified by use of a solvent when necessary.

Exemplary solvents which can be suitably used for the purification include methanol, ethanol, isopropyl alcohol and other alcoholic solvents; benzene, toluene, xylene and other aromatic hydrocarbon based solvents; dichloromethane, chloroform, dichloroethane, chlorobenzene and other halogenated hydrocarbon based solvents; diethyl ether, tetrahydrofuran and other ether based solvents; methyl isobutyl ketone, di-isobutyl ketone and other ketone base solvents; and a mixture of these solvents.

The invention will hereinafter be illustrated further in detail by way of examples.

EXAMPLE 1

To a 500 ml reaction vessel, 21.5 g of 2-[4,4'-bis(dimethylamino) benzhydryl]-5-dimethylaminobenzoic acid having a purity of 97.0% was charged and 250 g of water was added. To the dispersion thus obtained, 21.5 g of activated carbon; SHIRASAGI-C (manufactured by Takeda Chemical Ind. Co.) and 2.0 g of a 49% aqueous NaOH solution were added and stirred at 90 to 95° C. Through the reaction system thus obtained air was blown for 9 hours at a rate of 400 ml/min. After finishing the reaction, the reaction mass was filtered and the obtained cake was slurried in water, and completely dissolved by adding 19.5 g of a 36% aqueous HCl solution. Thereafter, the activated carbon was filtered. The filtrate was neutralized to pH7.0 with a 49% aqueous NaOH solution. The precipitated crystals were filtered, washed and dried to obtain 20.1 g of 3,3-bis(4-dimethylaminophenyl)-6-dimethylaminophthalide. The yield was 95.4%. Formation of by-product in the reaction was 1.5%. Selectivity of reaction was 98.4%.

EXAMPLE 2

To a 500 ml autoclave, 17.1 g of 2-[4,4'-bis(dimethylamino) benzhydryl]-5-dimethylaminobenzoic acid was charged and dispersed by adding 150 g of water. To the dispersion obtained, 3.4 g of activated carbon; SHIRASAGI-C and 1.63 g of a 49% aqueous NaOH solution were added and reacted at 100° C. for 3 hours under increased air pressure of 15 kg/cm². After finishing the reaction, the reaction mass was treated by the same procedures as carried out in Example 1 to obtain 16.1 g of desired 3,3-bis(4-dimethylaminophenyl)-6-dimethylaminophthalide. The yield was 95%. Formation of by-product in the reaction was 1.3%. Selectivity of reaction was 98.7%.

Comparative Example 1

The same procedures as Example 1 were carried out except that activated carbon catalyst was replaced by 1.2 g of copper sulfate 5 hydrate. 3,3-Bis(4-dimethylaminophenyl)-6-dimethylaminophthalide thus obtained was 19.1 g. The yield was 83.2%. Formation of by-product in the reaction was 6.0%. Selectivity of reaction was 90.2%.

Comparative Example 2

The same procedures as Example 1 were carried out except that activated carbon and the 49% aqueous NaOH solution were not used. After blowing air for 7.5 hours, almost no progress of the reaction was observed.

Comparative Example 3

The same procedures as Example 1 was carried out except that activated carbon was omitted. After blowing air for 24 hours, almost no progress was observed in the reaction. Thus, the reaction was terminated and the post treatment was carried out. 3,3-Bis(4-dimethylaminophenyl)-6-dimethylaminophthalide thus obtained was 11.2 g. The yield was 53%.

The above examples and comparative examples show that the reaction for preparing the phthalide compounds by oxidizing the leuco compounds in the invention can smoothly proceed in the presence of activated carbon. The oxidization of the leuco compound is remarkably slow when the reaction is carried out in a neutral reaction medium and in the absence of the catalyst. The reaction can proceed by use of a oxidation accelerating catalyst as shown in comparative Example 1. However, in order to manufacture phthalide compounds in industry by oxidation of leuco compounds, the problems of waste water disposal, further acceleration of selectivity of the reaction and inhibition of formation of by-product have been not yet sufficiently solved in the techniques relevant to the invention.

As illustrated in Comparative Example 1, the oxidizing reaction can proceed by use of an oxidation accelerating catalyst. However, more by-product is formed and selectivity is lower, and moreover, there is the problem of waste water disposal for removal of the oxidation accelerating catalyst eluted in the solution after reaction.

These problems can be eliminated by carrying out the oxidizing reaction in the presence of an activated carbon as illustrated in Examples 1 and 2, and the amount of such a by-product shown in Comparative Example 1 is reduced, and the reaction proceeds selectively, and furthermore the problems of waste water disposal can be eliminated.

The process of the invention which has made possible preparation of phthalide compounds within a short time and in high selectivity and high yield and can eliminate disposal problems of the residual reaction accelerator is very valuable in industry.

What is claimed is:

1. A preparation process of a phthalide compound represented by the formula (1):

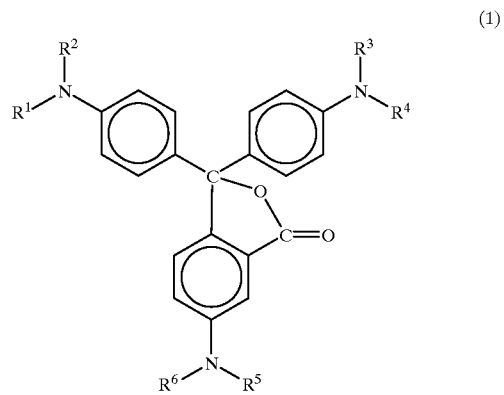

wherein $R^1$, $R^2$, $R^3$, $R^4$, $R^5$ and $R^6$ are individually an alkyl group, and $R^1$ and $R^2$, $R^3$ and $R^4$, and $R^5$ and $R^6$ can respectively bond to each other to form a heterocyclic ring together with a nitrogen atom, said process comprising oxidizing a triphenylmethane compound represented by the formula (2):

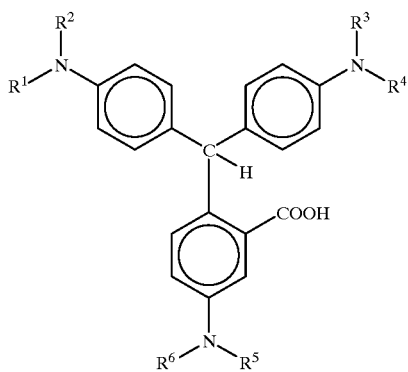

(2)

wherein $R^1$, $R^2$, $R^3$, $R^4$, $R^5$ and $R^6$ are individually an alkyl group, and $R^1$ and $R^2$, $R^3$ and $R^4$, and $R^5$ and $R^6$ can respectively bond to each other to form a heterocyclic ring together with a nitrogen atom, by an oxidizing agent in an aqueous solvent in the presence of activated carbon.

2. A preparation process of a phthalide compound according to claim 1 wherein the oxidizing agent is one or more agents selected from air, oxygen, hydrogen peroxide, and a mixture of oxygen with an inert gas.

3. A preparation process of a phthalide compound according to claim 1 wherein the aqueous solvent includes an acid or a base.

4. A preparation process of a phthalide compound according to claim 1 wherein the aqueous solvent includes a base.

5. A preparation process of a phthalide compound according to claim 4 wherein the base is sodium hydroxide.

6. A preparation process of a phthalide compound according to claim 2 wherein the oxidizing agent is air.

7. A preparation process of a phthalide compound according to claim 1 wherein the phthalide compound is 3,3-bis(4-dimethylaminophenyl)-6-dimethylaminophthalide.

* * * * *